United States Patent
Carter et al.

[11] Patent Number: 5,869,091
[45] Date of Patent: Feb. 9, 1999

[54] VESICLE FORMULATION

[75] Inventors: Katharine Christine Carter, Edinburgh; Alan James Baillie, Helensburgh; Denise Margaret Williams, Ardrossan, all of United Kingdom

[73] Assignee: University of Strathclyde, Glasgow, United Kingdom

[21] Appl. No.: 750,925

[22] PCT Filed: Aug. 7, 1995

[86] PCT No.: PCT/GB95/01859

§ 371 Date: Feb. 26, 1997

§ 102(e) Date: Feb. 26, 1997

[87] PCT Pub. No.: WO96/04890

PCT Pub. Date: Feb. 22, 1996

[30] Foreign Application Priority Data

Aug. 10, 1994 [GB] United Kingdom .................... 9416149

[51] Int. Cl.⁶ ............................ A61K 51/00; A61K 9/127
[52] U.S. Cl. ...................... 424/450; 424/1.21; 424/489; 424/490; 424/498; 424/502
[58] Field of Search .................................. 424/1.21, 450, 424/489–502

[56] References Cited

U.S. PATENT DOCUMENTS

| | | | |
|---|---|---|---|
| 3,999,071 | 12/1976 | Siffert et al. | 250/370 |
| 4,190,486 | 2/1980 | Kyle | 156/601 |
| 4,692,782 | 9/1987 | Seki et al. | 357/29 |
| 4,996,432 | 2/1991 | Saitou | 250/370.01 |
| 5,262,947 | 11/1993 | Boudan et al. | 364/413.24 |
| 5,315,506 | 5/1994 | Wang et al. | 364/413.19 |
| 5,653,970 | 8/1997 | Vermeer | 424/70.24 |

FOREIGN PATENT DOCUMENTS

| | | |
|---|---|---|
| 0 193 414 A2 | 3/1986 | European Pat. Off. . |
| 0 318 211 A1 | 11/1988 | European Pat. Off. . |
| 43 41 472 A1 | 12/1993 | Germany . |
| 63-14479 | 1/1988 | Japan . |
| 3-248578 | 6/1991 | Japan . |
| WO 91/04731 | 4/1991 | WIPO . |

OTHER PUBLICATIONS

E.N. Arkad'eva, et al., Possible Use of Cadmium Telluride for Detection of Pulsed X–Rays in Medical Tomography, Sov. Phys. Tech. Phys.26(9), Sep. 1981, pp. 1122–1125.

K. Zanio, et al., CdTe Detectors from Indium–Doped Tellurium–Rich Solutions, IEEE Trans. Nucl. Sci. NS21, 1974, pp. 315–321.

P. Hoschl, et al., Preparation of Cadmium Telluride Single Crystals for Nuclear Detectors, Czech. J. Phys. B., 1975, pp. 585–596a.

R.O. Bell, et al., Cadmium Telluride, Grown from Tellurium Solution, as a Material for Nuclear Radiation Detectors, Phys. Stat. Sol. (A), 1970, pp. 375–387.

Patent Abstracts of Japan, E Field, vol. 18, No. 406, issued Jul. 28, 1994; The Patent Office Japanese Government, p. 41 E 1585; & JP,A,06 120 549 (SHIMAZ DU CORP.).

(List continued on next page.)

*Primary Examiner*—Thurman K. Page
*Assistant Examiner*—Kathryne E. Shelborne
*Attorney, Agent, or Firm*—Bell Seltzer Intellectual Property Law Group of Alston & Bird, LLP

[57] ABSTRACT

The invention provides an aqueous formulation comprising a pharmaceutically active agent present within vesicles suspended in an aqueous carrier. The invention resides in the finding that improved therapeutic efficacy can be achieved by providing the active agent both in the vesicles themselves and in the aqueous carrier vehicle. The invention provides a formulation which comprises: an aqueous vehicle; vesicles suspended in the aqueous vehicle; and a pharmaceutically active agent comprised within both the vesicles and the aqueous vehicle.

17 Claims, 4 Drawing Sheets

OTHER PUBLICATIONS

A. Rose, Concepts in Photoconductivity and Allied Problems, Interscience Publishers, London 1963, [section 8.3].

R.E. Braithwaite, et al., Solid State Electron, vol. 23, 1980, pp. 1091–1092.

E. Janik & R. Triboulet, Ohmic Contacts to P–Type Cadmium Telluride and Cadmium Mercury Telluride, J. Phys. D.: Appl. Phys., 16 (1983), pp. 2333–2340.

G.F. Knoll, Radiation Detection and Measurement, John Wiley and Sons, 2nd. Edition, 1989, pp. 349.

R.J. Fox, et al., Use of Guard–Ring Silicon Surface–Barrier Detectors in Beta Spectrometry, Rev. of Scientific Instruments, 1962, p. 757.

A. Breskin and R. Chechik, High Accuracy Imaging of Single Photoelectrons by Low–Pressure Multistep Avalanche Chamber. . . , Nucl. Inst. & Methods in Phys. Res. 227 (1984), pp. 24–28.

Nanse R. Kyle, Growth of Semi–Insulating Cadmium Telluride, J. ElectroChem. Soc.: vol. 118, No. 11, 1971, pp. 1790–1797.

B. Biglari, et al., Evolution of Resistivity Along Cl–Compensated THM Grown Cadmium Telluride Crystals, Phys. Stat. Sol. (a) 100, 1987, pp. 589–596.

A. Yekta Ozer et al.; *A Novel Drug Delivery System: Non–Ionic Surfactant Vesicles, Eur. J. Pharm. Biopharm.* 37(2):75–79 (1991).

FIG. 4

VESICLE FORMULATION

This application is a 35 U.S.C. 371 of PCT/GB95/01859 filed Aug. 7, 1995.

FIELD OF INVENTION

The present invention provides an aqueous formulation (especially an injectable formulation) comprising a pharmaceutically active agent present within vesicles suspended in an aqueous carrier. The formulation particularly though not exclusively contains a pentavalent antimony compound as active agent for the treatment of the parasite infection visceral leishmaniasis.

BACKGROUND

The first line drugs currently used for the treatment of visceral leishmaniasis are pentavalent antimony compounds such as sodium stibogluconate and meglumine antimoniate. These drugs due to their polar nature are inactive by the oral route and undergo rapid renal excretion following dosing by the parenteral route, which necessitates a multiple dosing regime. Compliance with such a regimen is difficult to achieve in remote areas such as the Sudan where visceral leishmaniasis is endemic and has reached epidemic proportions. Development of a vesicular formulation of such antimonial drugs could increase their efficacy, allowing both the number of doses and dose size to be lowered.

The constituents of a vesicular formulation can influence vesicle characteristics (e.g. stability, size, charge) and hence its suitability as a drug carrier system and depending on the intended usage the requirements of the formulation can be drug specific. In our previous studies using a murine model of visceral leishmaniasis we have shown that vesicle size is important since elimination of Leishmania parasites from deeper sites such as the spleen required the use of small, drug loaded vesicles. Incomplete removal of parasites from these sites results in relapse and probably underlies the 2–8% relapse rate reported after antimonial therapy.

Diverse non-ionic surfactants can be used to form vesicles with potential therapeutic applications such as drug delivery (Ozer et al., 1991) and immunological adjuvants (Brewer and Alexander, 1993). We have already demonstrated (Carter et al., 1989a,b) that stibogluconate loaded non-ionic surfactant vesicles are as effective as drug loaded liposomes for improving the treatment of experimental visceral leishmaniasis.

It is an object of the present invention to provide such a vesicle formulation of improved efficacy. This and other objects of the present invention will become apparent from the following description and examples.

STATEMENT OF INVENTION

Broadly stated, the present invention resides in the finding that improved therapeutic efficacy can be achieved by providing the active agent both in the vesicles themselves and also in the aqueous carrier vehicle.

Thus, the present invention provides a formulation which comprises:
  an aqueous vehicle;
  vesicles suspended in the aqueous vehicle, and
  a pharmaceutically active agent comprised within both the vesicles and the aqueous vehicle.

DETAILED DESCRIPTION

The presence of the pharmaceutically active agent in both the vesicle phase and the aqueous liquid phase improves the efficacy thereof. The concentration of active agent in the aqueous vehicle may be the same, greater or lower than the concentration thereof in the vesicles. For convenience, the aqueous vehicle containing the active agent will generally be that which is used to load the active agent into the vesicles, where such a method is used to introduce the active agent into the vesicles.

In principal, the vesicle may be formed in any manner known in the art and appropriate to the active-agent to be delivered. For example, vesicles can be formed using either a "homogenisation" method or a "freeze-dried" method, both methods being known in the art. In the homogenization method a required quantity of lipid material in a desired molar ratio can be processed in one of the following ways: Dry powders (i.e. lipid material) are hydrated with a solution of the active agent for entrapment at a desired temperature, in the range from 0° up to 150° C.) and homogenised at the required speed and for the required length of time to produce the desired vesicle characteristics. Alternatively the lipid material can be melted by the application of heat (e.g. temperature range 40°–150° C.) prior to hydration with the required solution at the necessary temperature. The suspension can then be homogenized at the required speed and for the required length of time to produce vesicles having desired characteristics.

Sodium stibogluconate vesicle suspensions can be produced using the homogenisation method outlined above by heating the vesicle constitutents, for example, at 135° C. The molten lipid can then be cooled to, for example 70° C. prior to hydration with 5 ml of preheated sodium stibogluconate solution. Vesicle size reduction is achieved by homogenising the sample for a fixed time interval at a specific temperature e.g. for 15 minutes at 70° C. on a Silverson mixer (sealed unit) or an Ultra-turrac (model T25) (homogeniser machine) operated at, for example, 8000 rpm.

In the freeze-dried method, a freeze dried preparation can be made in one of the following ways: The required quantity of vesicle constitutents in a desired molar ratio can be dissolved in an organic solvent (e.g. t-butyl alcohol) prior to filtration, for example, through a porous membrane (e.g. 0.2 mm). The surfactant solution can then be frozen and freeze-dried for the time required for complete removal of organic solvent. Resultant lyophilised product can then be hydrated with a solution of the active agent to be entrapped and shaken at the required temperature to produce a vesicle suspension. Alternatively, vesicle suspensions are produced by the homogenisation process described above, filtered through a porous membrane (e.g. 0.2 mm), and then lyophilised to remove the aqueous solvent. The resultant lyophilised product can then be hydrated with the required solution and shaken at the required temperature to produce a vesicle suspension.

The vesicles are preferably formed of a sterol such as cholesterol or ergosterol, together with a surfactant. If a non-ionic surfactant is used, it is generally necessary to include a charged species such as a fatty acid within the vesicle formulation in order to prevent clumping of the vesicles. Suitable charged species include dicetylphosphate, stearic acid and palmitic acid.

It has been found particularly advantageous to employ a non-ionic surfactant. This may be a mono, di-, tri- or poly (up to 10) glycerol mono- or di-fatty acid ester (e.g. a $C_{10}$–$C_{20}$ fatty acid ester) such as triglycerol monostearate; or may be a polyoxyethylene ether preferably comprising from 1 to 10 oxyethylene moieties with a $C_{10}$–$C_{20}$ normal or branched alkyl chain such as to provide a hydrophilic head portion and a hydrophobic tail portion.

It is now considered that vesicle formulations comprising a non-ionic surfactant, cholesterol and dicetyl phosphate or a fatty acid can be present in a molar ratio of 3–5: 1–4: 0–4 respectively.

Preferred vesicle formulations comprise a non-ionic surfactant, cholesterol and dicetyl phosphate or a fatty acid selected from stearic or palmitic acid and these are advantageously present in a molar ratio of 3–5: 2–4: 0–3 respectively.

The vesicle diameter determined as described herein has now been found to be in the range of from 100 to 2500 nm and may therefore be considerably larger than 1000 nm. Preferably the vesicle diameter lies in the range of from 100 to 1000 nm and more preferably from 200 to 600 nm. It has been surprisingly found that vesicles of diameter in excess of 800 nm are effective. Such vesicle formulations are particularly effective against infections of the liver, spleen and bone marrow, and this allows preferential targeting of the active agent.

The active agent is in principle any agent which may be effectively delivered in a vesicle suspension. Particular agents include sodium stibogluconate, meglumine antimoniate, pentamidine, antimicrobials such as aminoglycosides (e.g. paromomycin) and amphotericin B. Hydrophilic active agents will generally be soluble in the aqueous vehicle, whereas those of a lipophilic nature will generally be present in the vesicular bilayer. The concentration of active agent in the vesicle phase is generally from 0.01 to 10% wt/wt.

The formulation is generally prepared by forming a mixture of the vesicle components—usually by melting these together and allowing to cool. In order to produce a vesicle suspension an aqueous liquid containing the active agent may be added to the melted vesicle formulation (e.g. at a temperature of 70°–100° C.) followed by vigorous agitation. The vesicle suspension may be extruded through a porous membrane to modify the particle diameter. The formulation may be used as produced, or the concentration of active agent in the aqueous phase may be varied as required.

In a further aspect of the invention there is provided use of formulations according to the invention in the manufacture of a medicament for the treatment of disease, in particular in the treatment of visceral leishmaniasis. Naturally, the skilled addressee will appreciate that in a further aspect of the invention there is provided a method of treating disease, in particular visceral leishmaniasis which comprises administering a formulation according to the invention to a mammal, in particular to humans.

Embodiments of the invention will now be described by way of example only.

EXAMPLES SECTION 1

Materials

Sodium stibogluconate (Pentostam) equivalent to 0.32 mg $Sb^v$/mg was obtained from The Wellcome Foundation, UK. The following chemically defined surfactants were used in this study: Surfactant V (triglycerol monostearate) and Surfactant VI (hexaglycerol distearate), purchased from Blagden Chemicals Ltd., UK; Surfactants VII (diethylene glycol mono n-nexadecylether), Surfactant VIII (tetraethylene glycol mono n-hexadecylether), and Surfactant IX (hexaethylene glycol mono n-hexadecylether) purchased from Chesham Chemicals Ltd., UK. Antimony standards, trypan blue, dicetyl phosphate and ash free cholesterol were obtained from Sigma and blue dextran T-2000 was obtained from Pharmacia Biosystems Ltd., UK. All other reagents were of analytical grade. Vesicle size reduction was carried out by passage through polycarbonate membranes (Nucleopore) using an extruder (Lipex Biomembranes Inc.). Vesicle suspensions were sized by photon correlation spectroscopy using a Malvern Zetasizer 4 (Malvern Instruments Ltd., UK) according to the manufacturer's instructions.

Animals and Parasites

Age and sex matched eight-to-ten week old in-house-bred male or female BALB/c mice were used throughout the study. Leishmania donovani (strain MHOM/ET/67:LV82) was maintained by serial passage through in-house bred Golden Syrian hamsters (Mesocricetus Auratus, Carter et al. 1988). Mice were infected by intravenous injection (tail vein, no anaesthetic) with $1-2 \times 10^7$ Leishmania donovani amastigotes (described by Carter et al., 1988). The day of parasite administration was designated day 0 of the experiment.

Vesicle Formation

A stock vesicular melt was first prepared by mixing surfactant, cholesterol and dicetyl phosphate in a 5:4:1 molar ratio, heating the mixture at 150° C. for 5 minutes, and then allowing it to cool. 150 $\mu$mole of the solidified stock vesicular melt was heated in a boiling water bath until melted and then rapidly hydrated at 70° C. with 5 ml 0.5% w/v trypan blue solution (dye vesicles), phosphate buffered saline (PBS pH7.4) or 300 mM D-glucose ('empty' vesicles). Hydration was continued with vigorous agitation for 2 hours at 70° C. Some vesicle suspensions were then extruded 10 times through two 200 nm pore diameter polycarbonate membranes followed by extrusion through two 50 nm pore diameter membranes using a jacketed (70° C.) extruder to modify the vesicle diameter. In some experiments, free drug or free trypan blue was removed from vesicle suspensions by gel filtration using an 18×2.6 cm Sephadex G50 column with PBS or Tes/histidine/Saline (THS buffer, pH7.4) as the eluant. Tes is an abbreviation for N-tris[hydroxy methyl]methyl-2-aminoethanesulfonic acid. The void volume of the column was ascertained by passing blue dextran T-2000 solution through the column.

In the preparation of 'V/D' suspensions according to the invention, the gel filtration step for the removal of free drug was omitted and the drug loaded vesicles were kept in the drug solution used for hydration.

Vesicular suspensions were sized using laser photon correlation spectroscopy. Suspensions were stored at 4° C. and used within 3 days of preparation.

Antimony determination 0.1 ml of the vesicle suspension, disrupted by the addition of an eaual volume of propanol, was diluted 1/50 with distilled water and the amount of antimony (Sb species) present determined by comparison with standards (antimony standard solution) using flame atomic absorption spectrophotometry. The entrapment efficiency (as a %) for a vesicle preparation was determined using the equation:

$$\frac{\text{amount of antimony present } (Sb^v/\text{ml}) \times 100}{\text{amount of antimony in hydrating solution } (Sb^v/\text{ml})}$$

Drug treatment and determination of parasite numbers

Infected mice (5/treatment) were treated via the tail vein (without anaesthetic) on days 7 and 8 or days 14 and 15 with a 0.2 ml volume of either PBS, 'empty' vesicles, drug loaded vesicles (total antimony dose 0.64–2.42 mg $Sb^v$/Kg) 'V/D' suspensions according to the invention hydrated with stibogluconate at concentrations of 0.97, 2.5, 5 mg $Sb^v$/ml (total antimony dose: 17.2, 44.4 and 88.8 mg $Sb^v$/Kg respectively) or free stibogluconate solution (total antimony dose: 17.2, 44.4 and 88.8 mg $Sb^v$/Kg). Seven days after the first drug treatment, i.e. on day 14 to 21, parasite numbers (per 1000 host cell nuclei) in the liver, spleen and bone marrow of control and drug treated mice were determined (Carter et al., 1988). Leishman-Donovan units (LDU) were calculated per organ for the liver and spleen using the formula LDU= amastigote number per 1000 host cell nuclei×organ weight (g) (Bradley and Kirkley, 1977).

Presentation and statistical analysis of data

Parasite burdens or the spleen and liver are expressed as mean LDU/organ+standard error, whereas the bone marrow counts are expressed as mean number of parasites/1000 host cell nuclei±standard error. The mean percentage parasite suppression±standard error (SE) is also shown which was determined by comparing each experimental value with the relevant means control for a particular site. Parasite burdens were analysed using a Students' unpaired t test on the log 10 transformed data (LDU/organ for spleen and liver and number of parasites/1000 host cell nuclei for the bone marrow).

RESULTS

Vesicle formation

Presumptive evidence for vesicle formation was obtained from gel filtration of surfactant suspensions hydrated with trypan blue solution. On this basis, Surfactants V–IX all formed vesicles since the trypan blue migrated in two bands, the first of which appeared in the void volume (vesicle entrapped dye) and the second, with a much larger elution elution volume, represented the unentrapped trypan blue.

All five surfactants also formed vesicles upon hydration with PBS or glucose with mean diameters in the range 203–639 nm (Table 1). Under the conditions used Surfactant IX formed the smallest vesicles with either hydrating solution. Hydration with different concentrations of sodium stibogluconate solution produced similar sized vesicles in the case of Surfactants V, VI, VII and VIII, although Surfactant VI did not form vesicles when hydrated with stibogluconate solution equivalent to 33.3 mg $Sb^v$/ml. Under the same conditions (hydration with stibogluconate solution), Surfactant IX produced the largest vesicles (Table 1).

Extrusion through polycarbonate membranes had little effect on mean vesicle diameter and indeed seemed to increase mean diameter in the case of the Surfactant IX vesicle suspension (Table 1). Using drug-loaded Surfactant VIII vesicles, extrusion through membranes of decreasing pore size resulted in the production of vesicles with progressively larger means diameter (data not shown) whereas gel filtration decreased mean vesicle diameter (Table 1).

The entrapment efficiency of the vesicles produced using the five different surfactants and two different concentrations of sodium stibogluconate for hydration was determined. At the lower drug concentration (5 mg $Sb^v$/ml) all vesicle preparations entrapped approximately 1% of the antimony in the hydrating solution with little variation among formulations (0.73%–1.1%). Hydration with 33.3 mg $Sb^v$/ml resulted in variable entrapment efficiencies (0.14%–3.46%), with Surfactant IX vesicles giving the lowest and Surfactant VIII vesicles the highest entrapments.

Parasite suppression

Table 2 shows or comparison purposes the effects of vesicle suspensions without drug in the aqueous phase. FIGS. 1–4 show V/D suspensions according to the invention. Table 3 gives a comparison of efficacy of V/D suspensions including modified V/D suspensions where the concentration of drug in the aqueous vehicle is varied.

1) Comparison Results

Treatment of *L.donovani* infected mice with 'empty' (glucose-loaded) vesicles prepared using Surfactants V, VI, VII or IX had no suppressive effect on liver, spleen or bone marrow parasite burdens compared with relevant controls (data not shown). However treatment with 'empty' Surfactant VIII vesicles lowered parasite numbers in the liver (p<0.05) but had no significant effect on parasite numbers in the spleen and bone marrow compared with controls (data not shown).

Treatment with either extruded or non-extruded drug loaded vesicles (total drugdoses in the range 0.42–2.42 mg $Sb^v$/Kg) prepared from Surfactant V (data not shown) and from Surfactants VII, VIII and IX (Table 2) significantly suppressed liver parasite burdens compared with relevant controls (p<0.0005) but had no effect on bone marrow parasite numbers. In the spleen, only treatment with drug loaded Surfactant VIII vesicles (extruded or non-extruded) caused significant (p<0.005) suppression in parasite burdens. The variation in efficacy among the vesicular preparations could be attributed to differences in drug content which in turn reflects differences in entrapment efficiency. However the important factor was the increased efficacy of the vesicular drug compared to the free form. The suppression obtained with a total dose of 88.8 mg $Sb^v$/Kg free stibogluconate was significantly p<0.0005) lower than that achieved with the vesicular preparations (dose range 0.42–2.42 mg Sb$^v$/Kg) At a dose of 88.8 mg Sb$^v$/Kg, free stibogluconate treatment did not suppress spleen and bone marrow parasite burdens (Table 2).

2) Results of V/D Suspensions according to the invention

Figure 1:
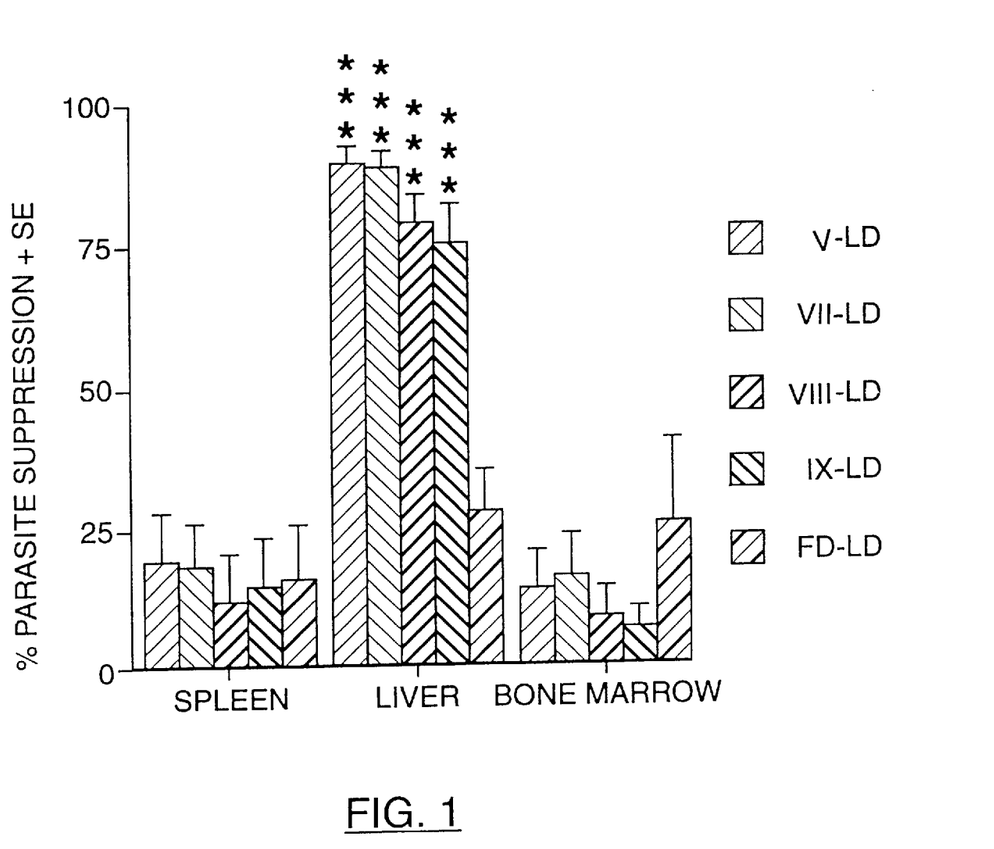
FIG. 1: Effect of treatment with surfactants V, VII, VIII or IX V/D stibogluconate suspensions (total dose/mouse 17.2 mg $Sb^v$/Kg) on spleen, liver and bone marrow parasite burdens of L.donovani infected mice.
Figure 2:
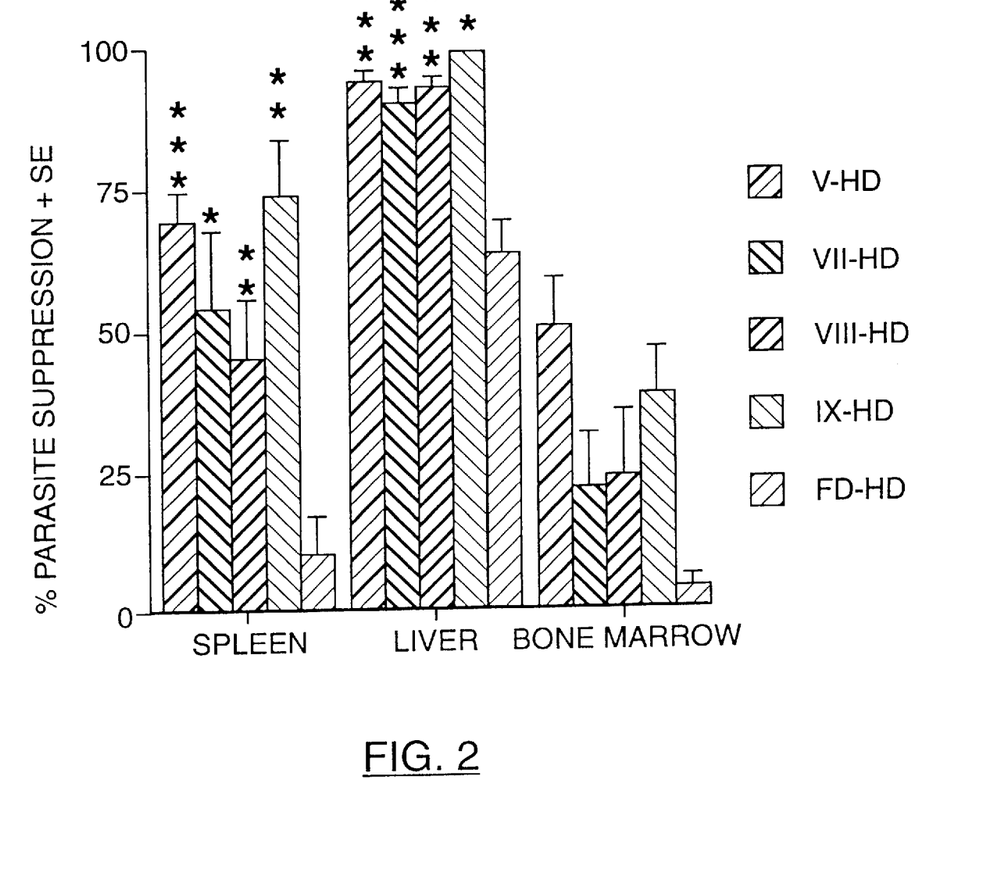
FIG. 2: Effect of treatment with surfactants V, VII, VIII or IX V/D stibogluconate suspensions (total dose/mouse 88.8 mg $Sb^v$/Kg, stibogluconate solution (total dose/mouse 88.8 mg $Sb^v$/Kg) or PBS (control) on spleen, liver and bone marrow parasite burdens of L. donovani infected mice.
Figure 3:
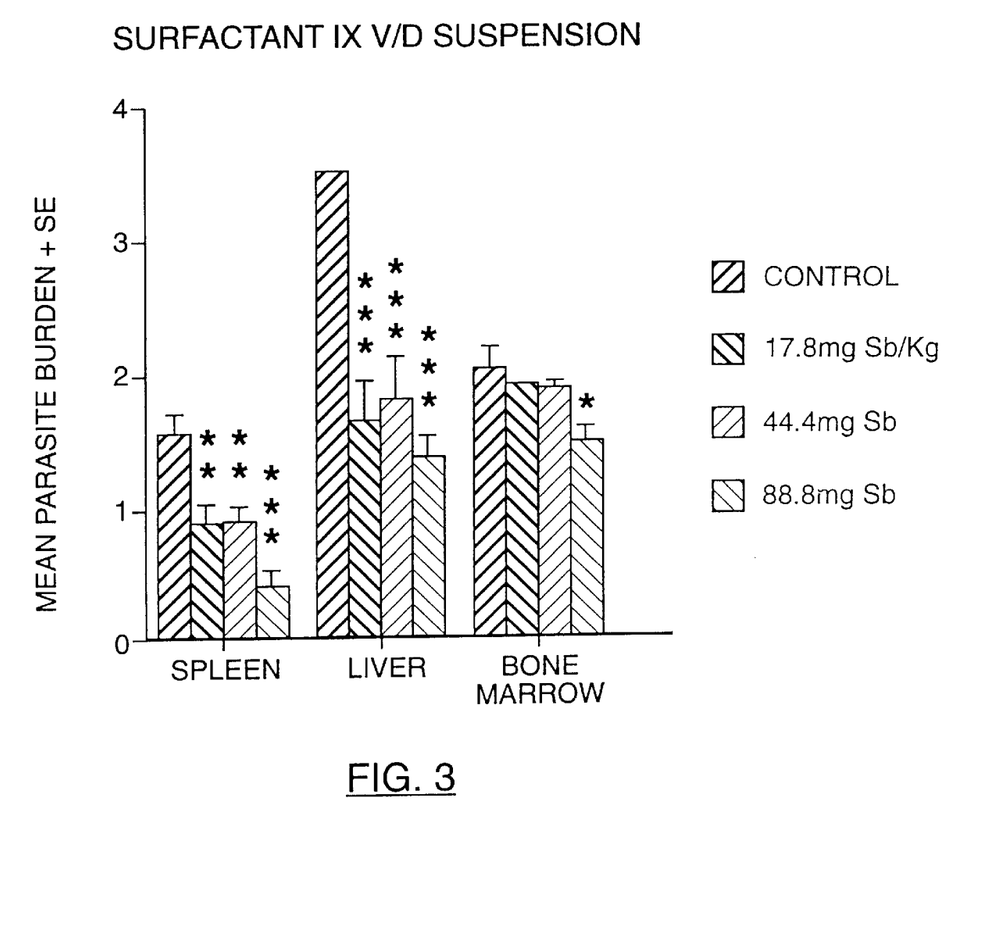
FIG. 3: Effect of treatment with surfactant IX V/D stibogluconate suspensions (total dose/mouse, 17.8, 44.4 or 88.8 mg $Sb^v$/Kg) or PBS (control) on spleen, liver and bone marrow parasite burdens of L.donovani infected mice.

FIG. 1 shows the effect of treatment with Surfactant V, VII, VIII or IX V/D stibogluconate suspensions according to the invention, FIG. 1 (total dose/mouse, 17.2 mg Sb$^v$/Kg) or FIG. 2 (total dose/mouse, 88.8 mg Sb$^v$/Kg), stibogluconate solution (total dose/mouse, 88.8 mg Sb$^v$/Kg) or PBS (control) on spleen, liver and bone marrow parasite burdens of *L.donovani* infected mice. Animals were treated on days 14 and 15 post-infection and sacrificed six days later. Student's test:*p<-0.05, p<0.005, *p<0.0005 compared with control values; and FIG. 3 shows the effect of treatment with Surfactant IX V/D stibogluconate suspensions according to the invention, (total dose/mouse, 17.8, 44.4 or 88.8 mg Sb$^v$/Kg), stibogluconate solution FIG. 4, (total dose/mouse, 17.8, 44.4, or 88.8 mg Sb$^v$/Kg), or PBS (control) on spleen, liver and bone marrow parasite burdens of *L.donovani* infected mice. Animals were treated on days 7 and 8 post-infection and sacrificed six days later. Student's test:* p<0.05, p<0.005, *p<0.0005 compared with control values.

V/D suspensions according to the invention prepared from Surfactants V, VI, VIII and IX, hydrated with 0.97 mg Sb$^v$/ml (total dose 17.2 mg Sb$^v$/Kg) elicited similar significant (p<0.0005) reductions in liver parasite numbers (FIG. 1). V/D suspensions prepared from these Surfactants but hydrated with 5 mg Sb$^v$/ml (total dose 88.8 mg Sb$^v$/Kg) elicited greater reductions in liver parasite numbers (FIG. 2). All of the V/D suspensions were more active than the equivalent dose of free drug against liver parasites.

At the lower dose level the V/D preparations had no significant effect against spleen or bone marrow parasites (FIG. 1) whereas all four V/D preparations at the higher dose level were active (p<0.01, FIG. 2) against parasites in the spleen, and Surfactant V and IX V/D suspensions were more active than Surfactant VII and VIII suspensions. only Surfactant V and Surfactant IX V/D suspensions (total dose 88.8 mg Sb$^v$/Kg) significantly suppressed bone marrow parasite numbers compared with controls (p<0.005, FIG. 2). At equivalent concentrations, free drug treatment had no significant effect on spleen or bone marrow parasites. The more effective Surfactant V and IX V/D suspensions contained the larger vesicles (mean diameters, 831±156 nm and 1030±257 nm respectively) than the lower activity Surfactant VII and VIII suspensions (mean diameters, 536±19 nm and 546±40 nm respectively).

Figure 4:
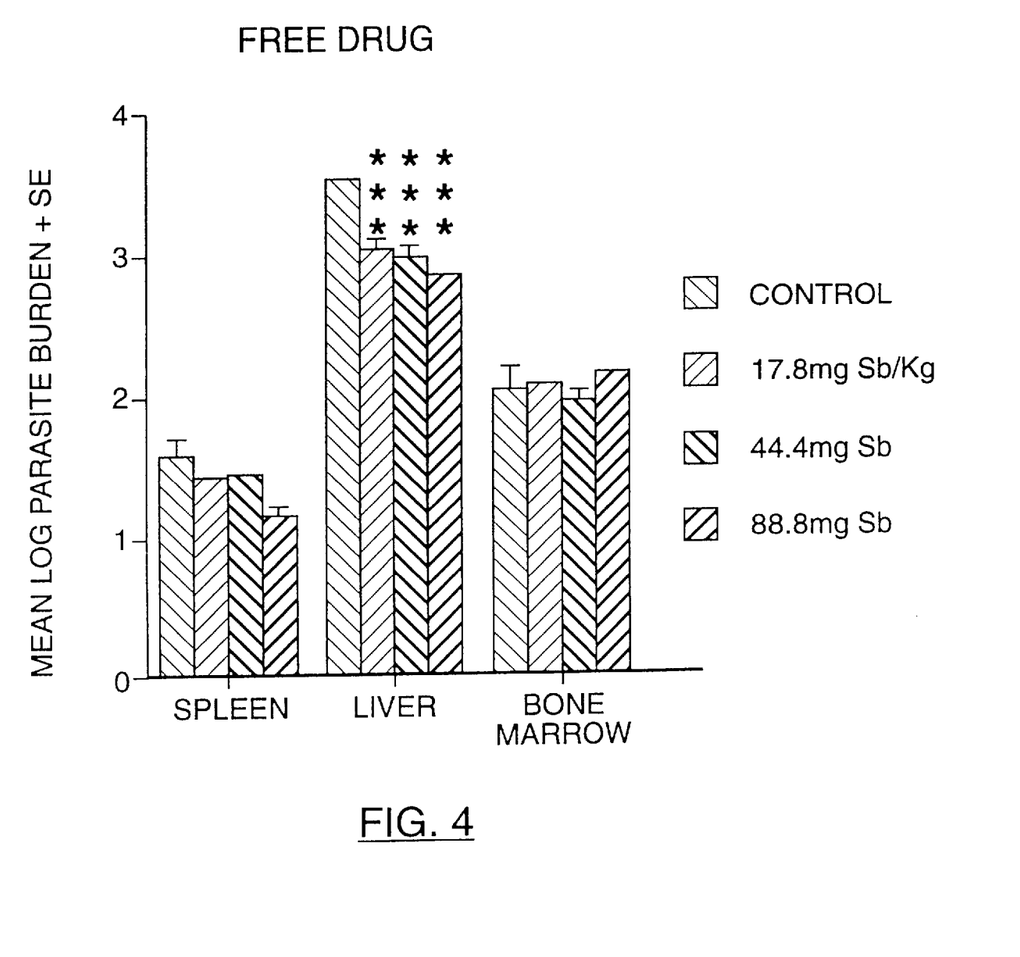
FIG. 4: Effect of treatment with free drug (stibogluconate) solutions (total dose/mouse 17.8, 44.4 or 88.8 mg $Sb^v$/Kg) or PBS (control) on spleen, liver and bone marrow parasite burdens on L. donovani infected mice.

Using a Surfactant IX V/D suspension, a dose dependent effect on spleen, liver and bone marrow parasite burdens was obtained (FIG. 3). Treatment with equivalent concentrations of free drug also had a dose dependent effect on liver *L.donovani* parasite burdens, a lesser effect on the parasites in the spleen, and no significant effect on bone marrow parasite numbers (FIG. 4).

TABLE 1

The mean hydrodynamic diameters (nm ± standard error) of various non-ionic surfactant vesicle suspensions (V to IX) formed by hydration of the appropriate surfactant: cholesterol:dicetyl phosphate mixture (5:4:1 molar) with solutions of glucose, PBS or sodium stibogluconate (SSG, concentration equivalent mg Sb$^v$/ml). Suspensions were either extruded or unextruded and in some cases were subjected to gel filtration (+).

| HYDRATING SOLUTION | V | VI | VII | VIII | IX |
| --- | --- | --- | --- | --- | --- |
| Unextruded | | | | | |
| glucose | 530 ± 25 | 399 ± 14 | 519 ± 26 | 524 ± 38 | 203 ± 6 |
| PBS | 639 ± 26 | 366 ± 11 | 312 ± 3 | 528 ± 19 | 295 ± 5 |
| SSG, 0.97 | 672 ± 27 | 280 ± 3 | 597 ± 69 | 461 ± 26 | 462 ± 13 |
| SSG, 5.0 | 562 ± 22 | 311 ± 4 | 521 ± 29 | 346 ± 17 | 630 ± 24 |
| SSG, 33.3 | 514 ± 27 | X | 447 ± 6 | 582 ± 29 | 653 ± 82 |
| Extruded | | | | | |
| PBS | 567 ± 24 | nd | 305 ± 1 | 630 ± 27 | 844 ± 151 |
| SSG, 0.97 | nd | nd | nd | nd | 782 ± 101 |
| SSG.50 | nd | nd | 541 ± 2 | 440 ± 11 | 932 ± 63 |
| SSG, 33.3 | nd | X | 579 ± 51 | 537 ± 20 | 968 ± 127 |
| Unextruded (+) | | | | | |
| SSG, 5.0 | 695 ± 34 | 307 ± 2 | 364 ± 7 | 212 ± 3 | 535 ± 25 |
| SSG, 33.3 | 517 ± 9 | X | 462 ± 29 | 444 ± 18 | 911 ± 44 |
| Extruded (+) | | | | | |
| SSG, 5.0 | nd | nd | 333 ± 4 | 334 ± 7 | 209 ± 6 |
| SSC, 33.3 | 950 ± 26 | X | nd | nd | nd | nd - not done: X - vesicles not formed.

TABLE 2

Suppression (% ± standard error) of parasite growth in viscera of *L. donovani* infected BALB/c mice treated with Surfactant VII, VIII or IX drug loaded vesicles. Animals were treated on days 7 and 8 post-infection with PBS (controls), vesicular drug (total $Sb^v$ dose/mouse, mg/Kg: unextruded, Surfactant VII, 0.42, Surfactant VIII, 2.42, Surfactant IX, 0.87; extruded, Surfactant VII, 0.75, Surfactant VIII, 2.42; Surfactant IX, 0.64) or free drug (total $Sb^v$ dose/mouse, mg/Kg, 88.8). On day 14 post-infection parasite burdens in the liver, spleen and bone marrow were determined. Values in parentheses show mean vesicle hydrodynamic diameters (nm ± standard error)

| | | % Suppression | | |
| --- | --- | --- | --- | --- |
| Surfactant | Extruded | Spleen | Liver | Bone Marrow |
| VII | Yes (333 ± 4) | 37 ± 8 | 94 ± 2 | 8 ± 8 |
| VII | No (366 ± 13) | 33 ± 13 | 82 ± 2 | 1 ± 1 |
| VIII | Yes (334 ± 8) | 52 ± 6 | 96 ± 1 | 10 ± 7 |
| VIII | No (212 ± 3) | 58 ± 5 | 96 ± 1 | 10 ± 7 |
| IX | Yes (209 ± 6) | 34 ± 14 | 93 ± 3 | 2 ± 2 |
| IX | No (535 ± 25) | 26 ± 11 | 90 ± 1 | 6 ± 4 |
| Free drug | | 29 ± 7 | 71 ± 6 | 15 ± 6 |

TABLE 3

% Parasite suppression in *Leishmania donovani* parasite burdens in the spleen, liver and bone marrow 6 days after treatment with the preparation shown.

| | Spleen | Liver | Bone Marrow |
| --- | --- | --- | --- |
| 'empty' Surfactant VIII vesicles | 7 | 21 | 8 |
| Surfactant VII vesicle suspension | | | |
| containing 23.8 μgSb$^v$/ml | 32 | 82 | 0 |
| containing 42.5 μgSB$^v$/ml | 37 | 94 | 0 |
| free drug (0.97 mgSb$^v$/ml ie. 970 μgSb$^v$/ml) | 20 | 30 | 11 |
| 'empty' Surfactant VIII vesicles mixed with free drug (0.97 mgSb$^v$/ml) | 5 | 61 | 20 |
| Surfactant VIII V/D suspension (0.97 mgSb$^v$/ml) | 19 | 92 | 31 |
| Surfactant VII modified V/D suspensions all washed and re-suspended in 0.97 mgSb$^v$/ml | | | |
| hydrated with 33.3 mgSb$^v$/ml | 92 | 99 | 96 |
| hydrated with 66.7 mgSb$^v$/ml | 92 | 99 | 92 |
| hydrated with 100 mgSb$^v$/ml | 66 | 99 | 37 |
| hydrated with 133 mgSb$^v$/ml | 58 | 98 | 31 |
| Surfactant VIII modified V/D suspensions all washed and re-suspended in 0.97 mgSb$^v$/ml | | | |
| hydrated with 33.3 mgSb$^v$/ml | 98 | 99 | 94 |
| hydrated with 66.7 mgSb$^v$/ml | 73 | 99 | 32 |
| hydrated with 100 mgSb$^v$/ml | 24 | 95 | 48 |
| hydrated with 133 mgSb$^v$/ml | 58 | 97 | 49 | note
'empty' vesicles - vesicles are made using glucose solution instead of drug
vesicle suspension - drug loaded vesicles washed to remove unentrapped drug, therefore only drug 'packets' given
V/D suspension - drug loaded vesicles are kept in the drug solution used to form them i.e. its a mixed preparation
modified V/D suspension - drug loaded vesicles produced and then washed to remove unentrapped drug (usually a very high drug concentration) and then the drug loaded vesicles are re-suspended in a dilute drug solution.

EXAMPLES SECTION 2

MATERIALS AND METHODS

Materials

Sodium stibogluconate (Pentostam) equivalent to 0.32 mg $Sb^v$/mg was obtained from The Wellcome Foundation, UK. Paromouycin sulphate was obtained from Sigma, UK. The following chemically defined surfactants were used in this study: Surfactant V (triglycerol monostearate) and Surfactant VI (hexaglycerol distearate), purchased from Blagden Chemicals Ltd., UK; Surfactant VII (diethylene glycol mono n-hexadecylether), Surfactant VIII (tetraethylene glycol mono n-hexadecylether), Surfactant IX (hexaethylene glycol mono n-hexadecylether) and Surfactant X (decaethylene glycol mono n-hexadecylether) purchased from Chesham Chemicals Ltd., UK. Dicetyl phosphate and cholesterol (ash free) were obtained from Sigma, UK and all other reagents were of analytical grade. Vesicle suspensions were sized using a Malvern Zetasizer 4 (Malvern Instruments Ltd., UK).

Animals and Parasites

Age and sex matched eight-to-ten week old in-house-inbred male or female BALB/c mice and age and sex matched in-house bred Golden Syrian hamsters (90–125 gm, Mesocricetus auratus) were used throughout the study. *Leishmania donovani* (strain MHOM/ET/67:LV82) was maintained by serial passage through in-house bred Golden Syrian hamsters (Carter et al. 1988, J. Pharm. Pharmacol., 40, 370–373). Mice (tail vein, no anaesthetic, Carter et al., 1988, J. Pharm. Pharmacol., 40, 370–373) or hamsters (jugular vein, anaesthetic, Carter et al. 1989, Int. J. Pharmaceutics 53, 129–137) were infected by intravenous injection with $1–2 \times 10^7$ *Leishmania donovani* amastigotes. The day of parasite administration was designated day 0 of the experiment.

Vesicle Formation a) Small scale production method

Sodium stibogluconate or paromycin non ionic vesicular (NIV) suspensions were prepared as described by Williams et al. (1995, J. Drug Targeting 3 1–7). Briefly, a stock melt was first prepared by mixing surfactant, cholesterol and dicetyl phosphate, palmitic or stearic acid in the desired molar ratio, heating the mixture at 135° C. for 5 minutes, and then allowing it to cool. 150, 750, 3750 or 6600 μmole of the solidified stock melt was melted over a boiling water bath and then rapidly hydrated at 70° C. with 5 ml sodium stibogluconate solution. Hydration was continued with agitation for 2 hours at 70° C. NIV suspensions, where drug loaded vesicles were maintained in the hydrating drug solution, were termed 'V/D' suspensions. In some cases the V/D suspensions were then processed to produce suspensions of drug loaded vesicles in a more dilute drug solution either by direct dilution of the V/D suspension with water or by removing the hydrating drug solution and resuspending the drug loaded vesicles present in the V/D suspension in a dilute drug solution. For example, a 6600 μmole V/D suspension was diluted with water with agitation to give a 750 μmole NIV suspension containing 3.75 mg $Sb^v$/ml. In order to remove the hydrating drug solution a V/D suspension was centrifuged for 50 minutes at 35,000 rpm (Beckman XL-90 Ultracentrifuge) and the vesicular pellet was resuspended in PBS (pH 7.4) or a fresh sodium stibogluconate solution (0.97 mg $Sb^v$/ml). After a further centrifugation for 50 minutes the pellet was finally resuspended in a fresh sodium stibogluconate solution (0.97, 2.31 or 5 mg $Sb^v$/ml) or PBS. In experiments the efficacy of these NIV suspensions was compared with that of the free drug used to resuspend the vesicular pellet (0.97, 2.31 or 5 mg $Sb^v$/ml).

b) Preparation of vesicle formulations using the 'homogenisation' method.

Vesicular constituents (surfactant, cholesterol and dicetyl phosphate, palmitic or stearic acid) in the desired molar ratio were heated to 135° C. The molten mixture was then cooled to 70° C. prior to hydration with 5 ml of preheated sodium stibogluconate solution. The suspension was then homogenised for 15 minutes at 70° C. on a Silverson mixer (sealed unit) or in a homogeniser Ultra-turrac (model T25), operated at 8000 rpm).

To determine the anziparasitic activity of 'drug free' vesicular formulations (glucose, PBS or water loaded ('empty')), vesicular suspensions were produced using the same methods described above. Vesicular suspensions were sized using laser photon correlation spectroscopy and stored at 4° C. All vesicular formulations were used within 3 days of preparation.

Antimony determination

Free drug was removed from vesicle suspensions by gel filtration, using an 18×2.6 cm Sephadex G50 column with PBS or pH7.4 Tes/Histidine/Saline buffer as eluant, prior to antimony content determination. 0.1 ml of vesicle suspension, disrupted by the addition of an equal volume of propanol, was diluted 1/50 with distilled water and the total amount of antimony present determined by comparison with standards (antimony standard solution, Sigma) using flame atomic absorption spectrophotometry.

Drug treatment

Infected mice or hamsters (5/group) were treated intravenously (tail vein for mice and jugular vein for hamsters) on day 7, 8 or 29 post-infection with 200 μl of the appropriate preparation: PBS (Control), a V/D suspension (2.25, 3.75 or 33.3 mg $Sb^V$/ml), a NIV suspension (antimony dose based on the concentration of the free drug solution present i.e. 2.25, 3.75 mg or 33.3 $Sb^V$/ml), glucose, PBS or water loaded vesicular suspensions) or stibogluconate solution (2.25, 3.75 or 33.3 mg $Sb^V$/ml). In some experiments mice were given either a single injection or two injections, 30 minutes apart, of PBS (controls) or a drug preparation on day 7 post-infection.

Determination of parasite numbers

Throughout, parasite numbers (per 1000 host cell nuclei) in the liver, spleen and bone marrow of control and drug treated animals were determined 7 or 50 days post-treatment (Carter et al., 1988, J. Pharm. Pharmacol., 40, 370–373). Leishman-Donovan units (LDU) were calculated per organ for the liver and spleen using the formula LDU=amastigote number per 1000 host cell nuclei x organ weight (g) (Bradley and Kirkley, 1977, Clin. Ex. Immunol., 30, 119–129).

Presentation and statistical analysis of data

The mean percentage parasite suppression±standard error (S.E.) is shown which was determined by comparing each experimental value with the relevant mean control for a particular site. Parasite burdens were analysed using a Students' unpaired t test on the log 10 transformed data (LDU/organ for spleen and liver and number of parasites/ 1000 host cell nuclei for the bone marrow).

RESULTS

TABLE 4

The effect of treatment (shown as mean % suppression±SE) with different sodium stibogluconate NIV formulations on parasite burdens of L. donovani infected BALB/c mice. Animals were treated intravenously on day 7 post-infection with 0.2 ml of one of the following: PBS (controls), free drug solution (2.25 mg $Sb^V$/ml) or NIV formulations and parasite numbers determined 7 days later. Vesicle suspensions (5500 μmole) were hydrated with 50 mg $Sb^V$/ml sodium stibogluconate and diluted with water to give a 750 μmole suspension containing 2.25 mg $Sb^V$/ml free drug solution/ml. The molar ratio of the constituents (Surfactant VIII: cholesterol: dicetyl phosphate or fatty acid) is shown in brackets. Vesicle suspensions were produced using the homogenisation method.

TABLE 4

| | % Suppression in parasite burdens ±SE | | |
|---|---|---|---|
| Treatment | Spleen | Liver | Bone Marrow |
| Free drug | 29 ± 10 | 3 ± 3 | 2 ± 2 |
| Dicetyl phosphate NIV (3:4:1) | 77 ± 6 | 99.5 ± 0.2 | 65 ± 17 |
| Stearic acid NIV (3:4:3) | 95 ± 2 | 99.9 ± 0.1 | 62 ± 9 |
| Palmitic acid NIV (3:4:3) | 98 ± 1 | 99.5 ± 0.2 | 67 ± 6 |

TABLE 5

The effect of treatment with Surfactant VIII sodium stibogluconate NIV suspensions (preparations 1, 2 or 3; 3:4:1 molar ratio) or stibogluconate solution (3.75 or 33.3 mg $Sb^V$/ml) on spleen, liver and bone marrow parasite burdens of L. donovani infected BALB/c mice. Preparation 1 was a 6600 μmole suspension hydrated with 33.3 mg $Sb^V$/ml drug solution and diluted with water to give a final drug concentration of 3.75 mg $Sb^V$/ml (concentration 750 μmole, drug dose/mouse equivalent to 33.3 mg $Sb^V$/Kg). Preparation 2 was prepared by centrifuging a fixed volume of a 750 μmole V/D suspension hydrated with 33.3 mg $Sb^V$/ml and resuspending the drug loaded vesicles in their original volume of a 2.31 mg $Sb^V$/ml free drug solution (concentration 750 μmole, drug dose/mouse equivalent to 20.5 mg $Sb^V$/Kg). Preparation 3 was a 750 μmole V/D suspension hydrated with 33.3 mg $Sb^V$/ml drug solution (drug dose equivalent to 296 mg $Sb^V$/Kg). Preparation 4 was a 750 μmole V/D suspension hydrated with PBS (empty vesicle suspension). Animals were given a single 200 μl dose on day 7 and sacrificed six days later. The suppression was calculated on the basis of the mean burden of control animals. Mean vesicle diameters±SE for the suspensions were: preparation 1, 2292±802 nm; preparation 2, 389±24 nm, preparation 3, 403±18 nm. Vesicle suspensions were produced using the small scale method.

TABLE 5

| | Mean % Suppression ± SE | | |
|---|---|---|---|
| Preparation | Spleen | Liver | Bone Marrow |
| Preparation 1 | 100 ± 0 | 99.9 ± 0.01 | 92 ± 5 |
| Preparation 2 | 100 ± 0 | 100 ± 0 | 100 ± 0 |
| Preparation 3 | 100 ± 0 | 100 ± 0 | 99 ± 1 |
| Preparation 4 free drug | 4 ± 4 | 33 ± 8 | 12 ± 8 |
| 3.75 mg $Sb^V$/ml | 10 ± 6 | 23 ± 10 | 21 ± 11 |
| 33.3 mg $Sb^V$/ml | 7 ± 7 | 90 ± 6 | 27 ± 11 |

TABLE 6

The effect of treatment with sodium stibogluconate formulations on the parasite burdens of L.donovani infected hamsters. Hamsters were treated intravenously on day 7 (acute infection) or day 29 (chronic infection) post-infection with 0.2 ml PBS (controls), free drug (33.3 mg $Sb^V$/ml) or a surfactant VIII stibogluconate NIV formulation (3:4:1 molar ratio, 750 μmole hydrated with 33.3 mg $Sb^V$/nl drug solution). Animals were sacrificed 7 days post-treatment. Compared with control values p<0.01, *p<0.005. Vesicular suspensions were prepared using the homogenisation method.

TABLE 6

| Treatment | Mean % Suppression ( ± SE) | | |
|---|---|---|---|
| | Spleen | Liver | Bone marrow |
| Acute Infection | | | |
| Free drug | 65 ± 9** | 81 ± 8*** | 50 ± 16 |
| NIV formulation | 92 ± 5** | 98 ± 1*** | 94 ± 2*** |
| Chronic Infection | | | |
| Free drug | 48 ± 18 | 46 ± 20 | 28 ± 17 |
| NIV formulation | 94 ± 3** | 98 ± 1*** | 91 ± 5** |

TABLE 7

The effect of treatment with paromomycin formulations on spleen, liver and bone marrow parasite burdens of L.donovani infected BALB/c mice. Animals were given a single 200 µl dose of PBS (controls) or paromomycin solution (7.9 mg/ml) or a 50 µl dose of a Surfactantx paromomycin NIV SUSPENSION (5:4:2) molar ratio, 750 µmole)on day 7 post-infection and sacrificed six days later. The NIV formulation was prepared by diluting a 3750 µmole suspension hydrated with 39.5 mg/ml paromomycin 1:5 with water before use. The vesicle suspension was produced using the small scale method and the drug dose given to mice in mg/Kg is shown in brackets.

TABLE 7

| Preparation | Mean % Suppression ± SE | | |
|---|---|---|---|
| | Spleen | Liver | Bone marrow |
| Free drug (70.2) | 20 ± 5 | 20 ± 14 | 20 ± 7 |
| NIV formulation (17.6) | 20 ± 20 | 66 ± 12 | 16 ± 8 |

REFERENCES

Bradley, D. J., Kirkley, J. (1977) Regulation of Leishmania populations within the host.I The variable course of Leishmania donovani infections in mice. Clin. Ex. Immunol., 30, 119–129.

Brewer, J. M., Alexander, J. (1993) The adjuvant of non-ionic surfactant vesicles (niosomes) on the BALB/c humoral response to bovine serum albumin. Immunol., 75, 570–575.

Carter, K. C. et al. (1989) Int. J. Pharmaceutics 53, pp129–137.

Carter, K. C., Baillie, A. J., Alexander, J., Dolan, T. F. (1988) The therapeutic effect of sodium stibogluconate in BALB/c mice infected with L. donovani is organ dependent. J. Pharm. Pharmacol., 40, 370–373.

Carter, K. C., Dolan, T. F., Baillie, A. J., Alexander, J. (1989a) The limitations of carrier mediated sodium stibogluconate chemotherapy in a BALB/c mouse model of visceral leishmaniasis in 'Liposomes in the therapy of infectious diseases and cancer' Lopez-Berestein G. and Fiddler I. J. (eds.), Alan R. Liss Inc., pp215–226.

Carter, K. C., Dolan, T. F., Alexander, J., Baillie, A. J., McColgan, C. (1989b) Visceral leishmaniasis; drug carrier system characteristics and the ability to clear parasites from the liver, spleen and bone marrow in Leishmania donovani infected BALB/c mice. J. Pharm. Pharmacol., 41, 87–91.

Ozer, A. Y., Hincal, A. A., Bouwstra, J. A. (1991) A novel drug delivery system: non-ionic surfactant vesicles. Eur. J. Pharm. Biopharm., 37, 75–79.

Williams, D. M., et al. (1995) J. Drug Targeting 3, pp1–7.

We claim:

1. A formulation comprising;
   (i) an aqueous vehicle;
   (ii) vesicles comprising a non-ionic surfactant, a sterol and a charged species suspended in the aqueous vehicle; and
   (iii) a pharmaceutically active agent located within both the vesicles and the aqueous vehicle.

2. A formulation according to claim 1 wherein the non-ionic surfactant is selected from mono-, di-, tri-, or poly (up to 1) glycerol mono- or di-fatty acid esters and a polyoxyethylene ether.

3. A formulation according to claim 2 wherein the non-ionic surfactant is selected from the group consisting of polyoxvethylene ethers, and polyolvalycerol fatty acid esters having from 1 to 10 glycerol units and from 1 to 2 fatty acid units.

4. A formulation according to claim 1 wherein the vesicle diameter lies in the range of from 100 to 2500 nm.

5. A formulation according to claim 1 wherein the vesicle diameter lies in the range of from 100 nm to 1000 nm.

6. A formulation according to claim 1 wherein the vesicle diameter lies in the range of from 200 nm to 600 nm.

7. A formulation according to claim 1 wherein the non-ionic surfactant, sterol and charged species are present in a molar ratio of 3–5: 1–4: 0–4 respectively.

8. A formulation according to claim 1 wherein the non-ionic surfactant, sterol and charged species are present in a molar ratio of 3–5: 2–4: 0–3 respectively.

9. A formulation according to claim 8 wherein the sterol is cholesterol and the charged species is dicetyl phosphate.

10. A formulation according to claim 7 or claim 8 wherein the charged species is a fatty acid.

11. A formulation according to claim 10 wherein the fatty acid is selected from stearic acid and palmitic acid.

12. A formulation according to claim 11 wherein the fatty acid is selected from the group consisting of stearic acid and palmitic acid.

13. A formulation according to claim 2 wherein the pharmaceutically active agent is selected from the group consisting of sodium stibogluconate, meglumine antimonate, pentamidine and antimicrobials.

14. A method for the treatment of disease comprising administering to a subject in need thereof a formulation according to claim 1 in an effective disease-combatting amount.

15. A method for the treatment of leishmaniasis comprising administering to a subject in need thereof a formulation according to claim 11 in an effective leisbmaniasis-combatting amount.

16. A formulation according to claim 13 wherein the antimicrobials are selected from the group consisting of aminoglycosides and amphotericin B.

17. A formulation according to claim 16 wherein the aminoglycoside is paromomycin.

* * * * *

UNITED STATES PATENT AND TRADEMARK OFFICE
CERTIFICATE OF CORRECTION

PATENT NO. : 5,869,091

DATED : February 9, 1999

INVENTOR(S) : Carter et al.

Page 1 of 2

It is certified that error appears in the above-identified patent and that said Letters Patent is hereby corrected as shown below:

On the title page: Item [56]

In References Cited, U.S. PATENT DOCUMENTS, insert --4,721,612 1/1988 Janoff et al.; 5,679,355 10/1997 Alexander et al.; 5,700,679 12/1997 Wright--.

FOREIGN PATENT DOCUMENTS, line 2, "11/1988" should read --5/1989--; line 3, "12/1993" should read --6/1995--.

Column 14, in claim 3, line 20, " claim 2" should read --claim 1--; line 22 "polyoxvethylene" should read --polyoxyethylene--; and "polyolvalycerol" should read --polyglycerol--.

Column 14, in claim 4, line 26, "100" should read --100nm--.

Column 14, lines 41 and 42, delete "11. A formulation according to claim 10 wherein the fatty acid is selected from stearic acid and palmitic acid."

Column 14, line 43, the claim number "12." should read --11.--; "according to claim 11" should read --according to claim 10--.

Column 14, line 46, the claim number "13." should read --12.--; the "according to claim 2" should read --according to claim 1--.

UNITED STATES PATENT AND TRADEMARK OFFICE
CERTIFICATE OF CORRECTION

PATENT NO. : 5,869,091
DATED : February 9, 1999
INVENTOR(S) : Carter et al.

It is certified that error appears in the above-identified patent and that said Letters Patent is hereby corrected as shown below:

Column 14, line 50, the claim number "14." should read --13.--.

Column 14, line 54, the claim number "15." should read --14.--; line 56, "according to claim 11" should read --according to claim 1--; "leisbmaniasis-" should read --leishmaniasis--.

Column 14, line 58, the claim number "16." should read --15.--; "according to claim 13" should read --according to claim 12--.

Column 14, line 61, the claim number "17." should read --16.--; "according to claim 16" should read --according to claim 15--.

Signed and Sealed this

Fourth Day of July, 2000

Attest:

Q. TODD DICKINSON

*Attesting Officer*          *Director of Patents and Trademarks*